United States Patent [19]

Morgan et al.

[11] 4,402,214
[45] Sep. 6, 1983

[54] FILTER ELEMENT TEST METHOD AND APPARATUS

[75] Inventors: Morgan H. Morgan, Greeneville, Tenn.; Pamela T. Anders, Berkley, Mich.

[73] Assignee: Facet Enterprises, Inc., Tulsa, Okla.

[21] Appl. No.: 252,484

[22] Filed: Apr. 8, 1981

[51] Int. Cl.³ ............................................. G01M 3/20
[52] U.S. Cl. ........................................ 73/40.7; 73/38
[58] Field of Search ................... 73/40.7, 40, 38, 61 R

[56] References Cited

U.S. PATENT DOCUMENTS

| 2,157,135 | 5/1939 | Little et al. | 73/38 |
| 2,819,608 | 1/1958 | McLaren et al. | 73/38 |
| 2,833,140 | 5/1958 | Austen et al. | 73/38 |
| 3,293,431 | 12/1966 | Bennett et al. | 73/38 X |
| 3,736,790 | 6/1973 | Pontello | 73/40.7 X |
| 4,055,075 | 10/1977 | Allan et al. | 73/40.7 |
| 4,324,568 | 4/1982 | Wilcox et al. | 73/40.7 X |

FOREIGN PATENT DOCUMENTS 2618914  11/1977  Fed. Rep. of Germany ....... 73/40.7

OTHER PUBLICATIONS

Burchsted et al., *Design, Construction, and Testing of High-Efficiency Air Filtration Systems for Nuclear Application,* Published by Oak Ridge National Laboratory, Jan. 1970, pp. 7.1–7.13.

Fochtman, E. G. et al., *Nondestructive Test of Cartridge Filter Elements,* In Filtration & Separation, p. 608–610, Sep.–Oct. 1971.

Primary Examiner—James J. Gill
Assistant Examiner—Joseph W. Roskos
Attorney, Agent, or Firm—Remy J. VanOphem

[57] ABSTRACT

A filter testing device is disclosed wherein the ends of a filter element is clamped between resilient seals in a filter holder member. A dioctyl phthalate smoke generator generates smoke which is passed through the filter element. An annular sampler which is mounted between the top member and base member of the filter holder member is moved vertically along the axial length of the filter. The annular sampler has an annular cavity therein with a plurality of radial holes extending from the inner diameter to the annular cavity. A vacuum pump draws the sample from the annular cavity in the annular sampler into a forward light scattering particulate detector device wherein the quantity of smoke is measured on a meter.

25 Claims, 5 Drawing Figures

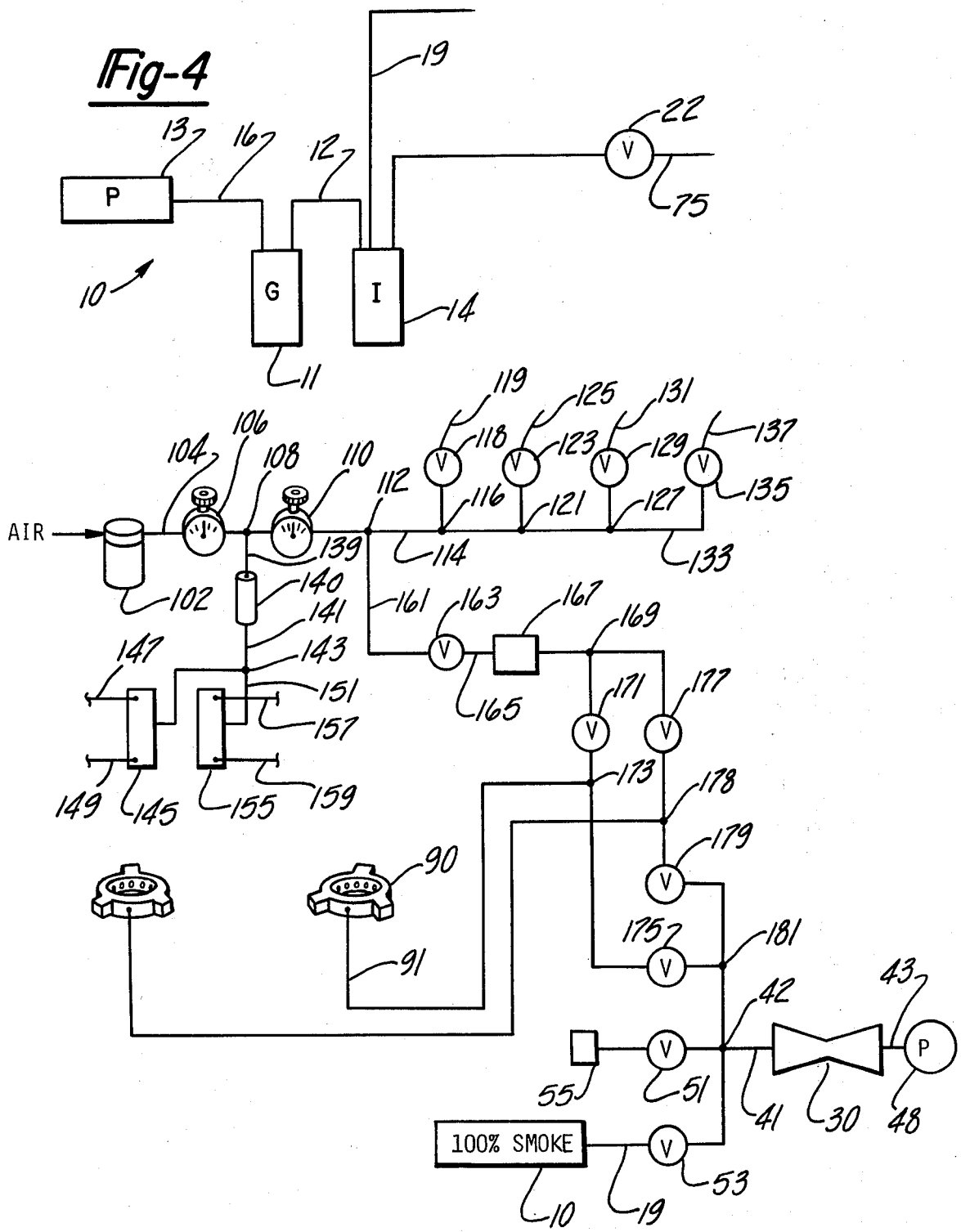

FILTER ELEMENT TEST METHOD AND APPARATUS

FIELD OF THE INVENTION

The present invention relates broadly to the manufacture of fluid filters and, more particularly, to the testing of filter elements for quality control.

BACKGROUND OF THE INVENTION

Filter elements normally require a very large surface area to permit a free flow of fluid therethrough. In addition, filter elements have a further requirement to permit the accumulation of a large quantity of foreign matter therein without restricting the flow of fluid excessively therethrough.

The normal range of pore sizes in a filter are such that foreign particles larger than a certain size cannot pass through the filter. When flaws, such as a ruptured element are present in a filter element, particles larger than the normal pore size range can pass through the filter and render the filter ineffective for its intended use. Thus, even a small rupture in a filter element is considered a failure and must be detected. Various prior art devices and methods have been devised to test filter elements for such flaws.

U.S. Pat. No. 1,395,247 to A. Abrams, issued Nov. 1, 1921, discloses an apparatus for generating hydrogen sulphide smoke and for applying this smoke to test the porosity of materials. Abrams determines the distribution of pores in the test material by first saturating the filter element with a litmus indicator. Abrams then passes the hydrogen sulphide smoke through the filter element and when the hydrogen sulphide passes through the filter, an indication will be shown on the litmus paper to show how the pores are distributed in the filter element. This test, however, is time consuming, complicated and could significantly reduce the lift of the filter element tested. In addition, Abrams' test method could pose a health hazard to the operator.

Finkelstein, in U.S. Pat. No. 2,072,872, issued Mar. 9, 1937, discloses an apparatus for testing filters utilizing smoke generated by directing atomized oil against an electrically heated plate. This smoke is then passed through the filter element being tested. The smoke passing through the filter element is measured by a light sensitive cell. This apparatus is also complicated and time consuming. In addition, it has been found that smoke particles generated by hydrocarbon oils have a tendency to agglomerate and, thus, there may be a wide variation in the size of smoke particles generated by this device. This can cause erratic, unrepeatable test results.

Another prior art filter testing device is disclosed in U.S. Pat. No. 2,819,608 issued to McLaren et al on Jan. 14, 1958, owned by the assignee of the present patent application. McLaren et al discloses an apparatus for testing the performance of filter elements by utilizing water and spherical glass beads having a known size distribution. A first beam of light is projected through the fluid before it passes through the filter element and a second beam of light is projected through the fluid after it passes through the filter element. The ratio of the amount of light scattered in the first and second beams provides an instantaneous indication of the relative density of the contaminant before and after passing through the filter element. Thus, McLaren's device provides a continuous measurement of the efficiency of the filter. However, this apparatus and method is also time consuming and may be harmful to the life of certain filters.

In U.S. Pat. No. 2,833,140 issued to A. E. W. Austen et al, on May 8, 1958, a filter testing apparatus utilizing air entrained dust is disclosed. Austen provides a chamber for accommodating a filter to be tested and then introduces air entrained dust into the chamber. Austen then provides a baffle means for promoting the deposition of the airborne dust and an inspectable surface on which such deposition takes place. This apparatus is also time consuming requiring a visual inspection of each filter element after the test. Therefore, the apparatus is not suitable for testing large quantities of filters as usually required for quality control purposes.

Tuttle, in U.S. Pat. No. 3,336,793 issued Aug. 22, 1967, discloses a filter test mechanism apparatus wherein a filter element is chucked on a rotatable spindle which is a piston rod of a fluid cylinder. Retraction of the piston rod by the piston deforms an elastic ring to hold the element firmly and to seal the open ends of the filter element. The filter is then immersed and rotated within a liquid bath to entirely coat the filtering area of the filter element. Then, pressure regulated gas is admitted into the interior of the filter. The interior of the filter element and a fluid pressure indicating instrument thus forms a closed system except for the pores of the filter element medium and any flaws present therein. Tuttle then measures the drop in pressure of this closed system so as to indicate leakage of the filter element. This device and mechanism is also not suitable for all types of media and may cause contamination of the filter element in certain applications. In addition, the method and apparatus is time consuming and not suitable for use in testing large numbers of filter elements.

Another apparatus and method for determining structural failure of filter elements is disclosed by A. J. Taylor et al in U.S. Pat. No. 3,608,354, issued Sept. 28, 1971. Taylor determines a failure in a filter element by sensing a drop in the pressure of fluid flowing through the filter. To accomplish this, a support is provided for a filter element and contaminated fluid is pumped from a reservoir to the filter element by means of a pump through a supply conduit. A drain conduit returns the fluid from the filter to the reservoir. The pressure of the fluid before entering the filter is indicated on a suitable pressure gage. A drop in pressure in the supply conduit is sensed by a differential pressure sensing device having opposite sides connected to the supply conduit near the filter element support. One side of the sensing device is connected directly by conduit to the supply conduit while the other side is connected to the supply conduit by means of a second conduit which has unidirectional flow means interposed in the conduit. The unidirectional flow means permits the free flow of fluid in the direction towards the sensing device but resists fluid flow in the opposite direction. When a rupture in a filter element under test occurs, a reversal in pressure creates a differential pressure across the pressure switch which causes the pump motor to stop and activates a solenoid of a bypass valve to open. Thus, the differential pressure switch indicates a rupture of the filter element. While this device is purported to be automatic in operation, it is time consuming and not suitable for testing large numbers of filter elements. In addition, this device may cause contamination of the filter element for certain types of filter media.

In summary, therefore, none of the known prior art devices provide an apparatus and method which is suitable for all types of filter media, which does not significantly reduce the life of the filter media and is suitable for testing large numbers of filters elements.

SUMMARY OF THE INVENTION

The present invention is directed to a device and method for testing filter elements which does not significantly reduce the life of the filter media, is suitable for testing large numbers of filter elements, is simple, in that, it does not require operator skill or judgment, and which is suitable for production line usage to test the quality of the filter elements.

The present invention provides a filter element testing device using particles entrained in air. The device includes a filter holder member and a mechanism mounted in the filter holder member for clamping the filter element therein. In addition, a mechanism is provided for passing particles entrained in air through the filter element. Finally, a mechanism is mounted transversely of the filter element to detect the particles entrained in air passing through the filter element.

The present invention also provides a method for testing a fluid filter element for defects. The method includes the steps of passing a test fluid having foreign particles entrained therein, through a filter element to be tested. Next, moving a probe adjacent to the periphery of and transversely across the longitudinal axis of the filter element to collect foreign particles passing through the filter element therein, and finally, measuring the concentration of particles collected by the probe.

It is, therefore, a primary object of the present invention to provide a method and apparatus for testing filter fluid elements for defects which is simple to operate, is suitable for testing large numbers of filter elements, is not detrimental to the capacity of the filter element and may be applied to a wide range of filter media.

It is yet still a further object of the present invention to provide a method and apparatus for testing fluid filter elements for defects utilizing homogeneous dioctyl phthalate smoke particles so as to provide a nondestructive filter element test, suitable for large numbers of filter elements, that is, quick, simple to operate, does not require operator skill to operate and is not detrimental to the capacity of the filter element.

It is yet still a further object of the present invention to provide a method and apparatus for testing fluid filter elements for defects by passing a test fluid having foreign particles entrained therein through the filter element to be tested by sampling along the transverse axis of the filter element to collect the foreign particles passing through the filter element and for measuring the concentration of particles collected by the probe, which is quick, simple to operate, is nondestructive and is not detrimental to the capacity of the filter element.

It is still yet a further object of the present invention to provide a method and apparatus for testing fluid filter elements for defects utilizing homogeneous dioctyl phthalate smoke particles of three microns or less which does not substantially reduce the capacity of the filter and yet provides a simple, inexpensive and quick test device which does not require operator skill.

These and other objects and advantages of the invention will become apparent upon reading the following detailed description and upon reference to the drawings.

BRIEF DESCRIPTION OF THE DRAWINGS

FIG. 4 is a schematic diagram of the smoke generator; and

FIG. 5 is a schematic diagram of the pneumatic system according to my invention.

DESCRIPTION OF THE PREFERRED EMBODIMENT

Figure 1:
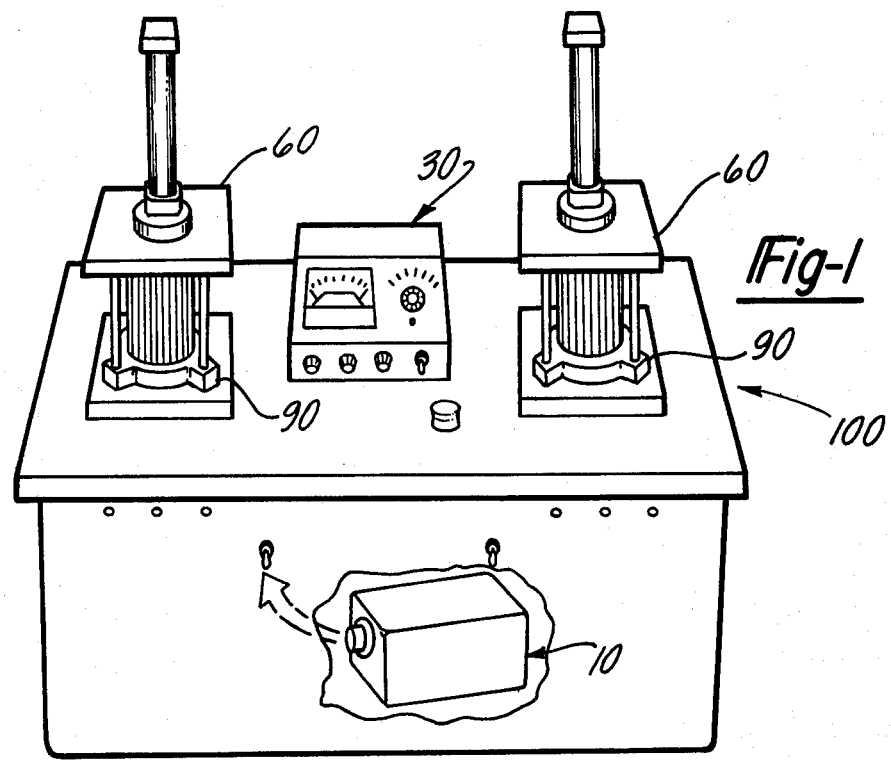
FIG. 1 is a perspective view of the apparatus according to my invention.

The apparatus of the present invention is generally designated by the numeral 100 as shown in FIG. 1. The apparatus 100 includes a smoke generator 10, a particulate detector device 30, a pair of filter holder members 60 and a pair of sampler members 90.

The smoke generator 10 produces a substantially homogeneous dioctyl phthalate or D.O.P. smoke by compressing liquid dioctyl phthalate and ejecting polydisperse D.O.P. smoke through two laskin type nozzles (not shown) into a stream of air. The resulting D.O.P. smoke produces a distribution of at least 99% of the particles sized less than 3.0 microns. Such a smoke generator is commercially available as a Model TDA-6A D.O.P. Aerosol Generator by Air Techniques, Inc. of Baltimore, Maryland. As shown in FIG. 4, the smoke generator 10 includes a generator 11 which is connected to an impactor 14 via a tube 12. The generator 11 has a reservoir (not shown) therein which holds a supply of D.O.P. liquid therein. The generator 11 compresses the D.O.P. fluid from the reservoir and ejects the pressurized D.O.P. fluid through two laskin type nozzles into a chamber (not shown) where the D.O.P. liquid is sprayed into a stream of air supplied by a pump 13 via a line 16 into the generator 11. Thus, the nozzles eject the D.O.P fluid into the chamber so as to produce a polydisperse D.O.P. aerosol. The D.O.P. in the chamber is then mixed with air which flows by the tube 12 to the impactor 14. The impactor separates those particles greater than 3.0 microns and permits the remaining D.O.P. smoke to flow out of the impactor by an outlet tube 19 as well as to a valve 22 and tube 75 for a purpose to be described later on herein. The particles greater than 3.0 microns are collected and returned back to the generator by a tube (not shown).

Figure 2:
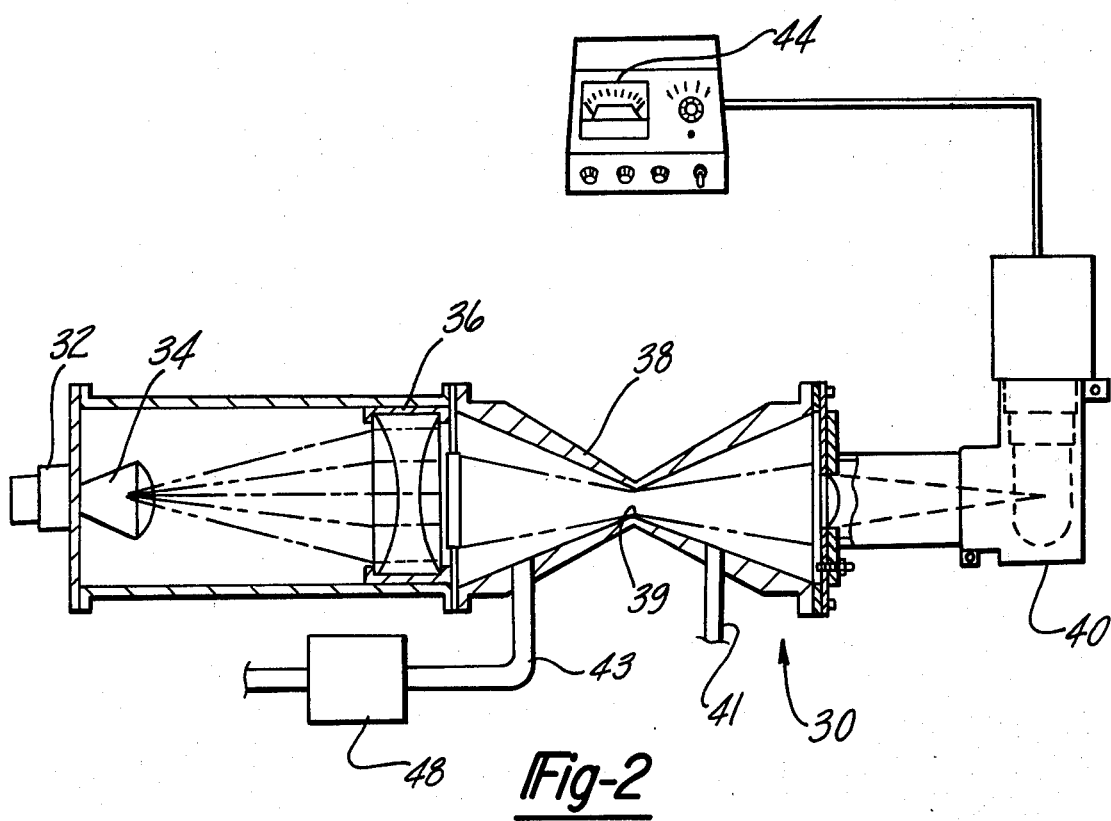
FIG. 2 is a schematic diagram of the detector.

As shown in FIG. 2, the particulate detector device 30 includes a forward light scattering chamber 32, a photo-multiplier tube 40, a meter 44 and a vacuum pump 48. The light scattering chamber 32 has a light source 34, a lens 36 and a black coated conical chamber 38. The light source 34 and lens 36 are mounted on one side of the conical chamber 38. On the opposite side of the conical chamber 38 is mounted a photo-multiplier tube 40. Interposed the one side and the opposite side of the chamber 38 is formed an aperture 39 which separates the chamber 38 into a first cell adjacent the photo-multiplier tube 40 and a second cell adjacent the light source lens 36. The first cell communicates with the second cell through the aperture 39. A first conduit 41 is connected to the first cell and a second conduit 43 is connected to the second cell. Thus, the first conduit 41, the first cell, aperture 39, the second cell and the second conduit 43 are interconnected for flow communication therebetween. Flow is induced through the second conduits 43, the conical chamber 38 and the first conduit 41 by means of the vacuum pump 48 which is connected to the second conduit 43. The photomultiplier tube 40 is connected to the meter 44 which will be described more fully hereinafter.

As best shown in FIG. 5, the first conduit 41 is connected to one leg of the cross 42. The other leg of the cross 42 is connected to a first solenoid valve 51 and the one branch of the cross 42 is connected to a second solenoid valve 53. The first solenoid valve 51 is connected to a high efficiency particulate filter member 55 which communicates with atmospheric air. The second solenoid valve 53 is connected to the outlet tube 19 to draw a quantity of D.O.P. smoke sample from the smoke generator 10 therein. This will be more fully discussed later on herein.

When operating the detector device 30, a sample to be analyzed is drawn from the first conduit 41 into the first cell of the chamber 38 by the vacuum pump 48. The sample thus passes through a beam of light emanating from the light source 34 through the lens 36. The light source is directed from one side of the conical chamber 38 through the aperture 39 towards the photo-multiplier tube 40. The light is reflected forwardly off any smoke particles in the sample and the light is then concentrated on the photo-multiplier tube 40. The resulting signal from the photo-multiplier tube 40 is fed into an amplifier circuit (not shown). The amplifier circuit processes the signal into linear readings on the meter 44. This results in a measurement of mass concentration of particulate matter in the air. Those skilled in the art will recognize that the meter 44 may be a dial and a needle but preferably, the meter is a digital readout device. A detector device 30 as heretofore described is commercially available as Model TEA-2D Particulate Detection Device by Air Techniques, Inc. of Baltimore, Maryland.

Figure 3:
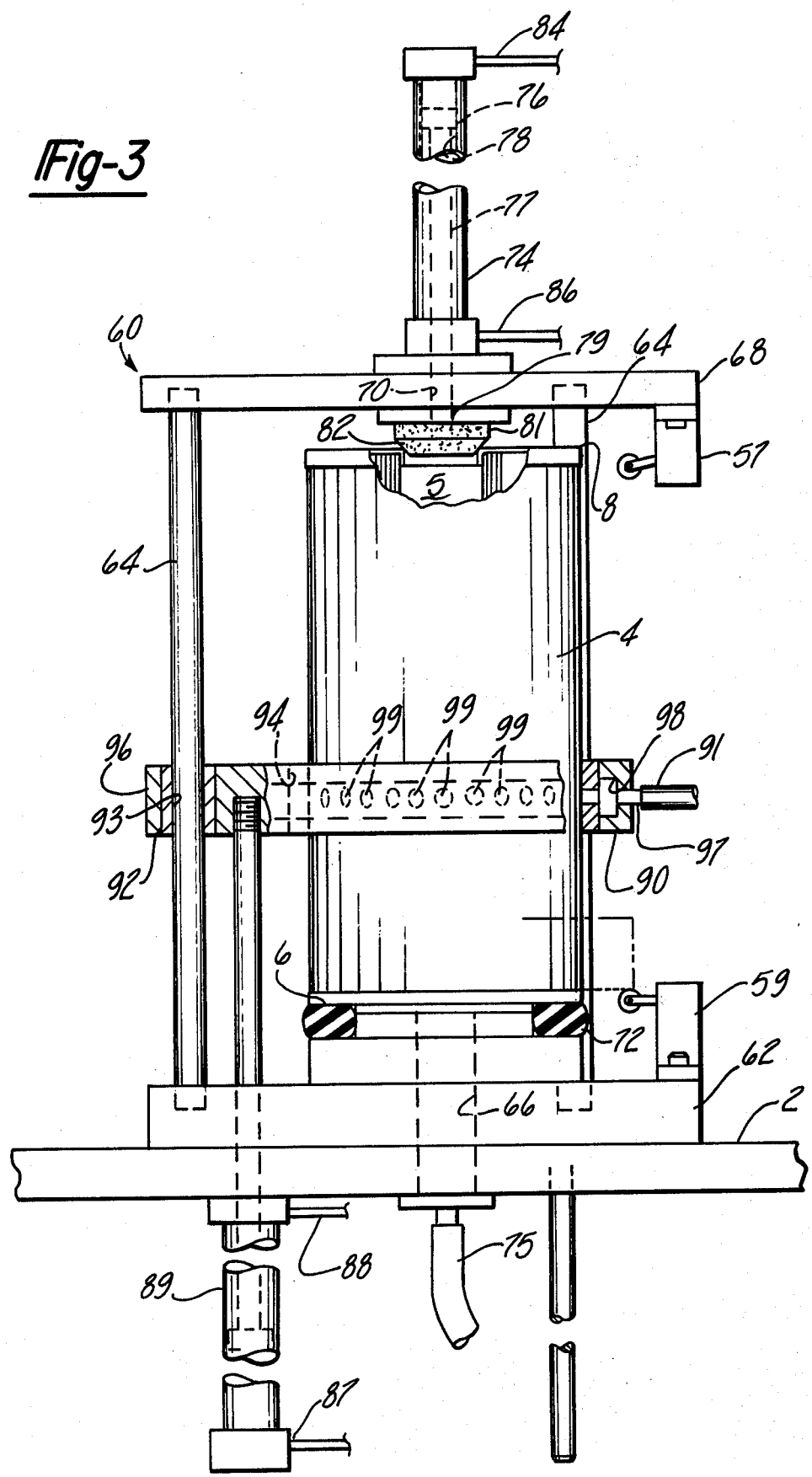
FIG. 3 is an enlarged perspective view of the filter holder member and sampler member with filter element in place.

As set forth above, the apparatus 100 includes a pair of filter holder members 60 which are identical to each other. Thus only one of the pair of filter holder members 60 will be described in detail. One of the filter holder members 60 of the present invention is disposed on a substantially flat horizontal surface 2 as shown in FIG. 3. Each of the filter holder members 60 includes a base member 62 which is suitably fastened by conventional screw means to the surface 2. A top member 68 is positioned above the base member 62. The top member 68 is connected to the base member 62 by three vertical support members 64 (only two shown in FIG. 3). The support members 64 are preferably equally spaced about an aperture 66 in the base member 62. The support members 64 are threadably connected at one end to the base member 62 and are threadably connected at the opposite end to the top member 68 so that the vertical difference between the top and bottom members 62, 68 respectively may be adjusted to accommodate various length filter elements 4 therebetween.

Centrally disposed around the aperture 66 is mounted a resilient seal member 72. The aperture 66 is connected to a conduit 75 for a purpose to be discussed more fully herein after.

The top member 68 also has an aperture 70 formed therein. On the top of the top member 68 is mounted a first air cylinder 74. The first air cylinder 74 is a double acting pneumatic piston 76 disposed within a bore 78 in the first air cylinder 74. The piston 76 is connected to one end of a rod 77. The other end 79 of the rod 77 extends through the aperture 70 in the top member 68 and is connected to a plate member 81 which has a resilient seal 82 mounted thereon. The seal 82 is provided to engage the top end 8 of the filter element 4 as will be discussed more fully herein after. The filter element further has a central passage 5 extending axially from the bottom end 6 to the top end 8.

The first air cylinder 74 has a first port 84 adjacent its opposite end. The first port 84 is connected to the bore 78 for flow communication therebetween. Additionally, a second port 86 is provided adjacent to the one end of the first air cylinder 74 which also communicates with the bore 78 for flow communication therebetween. Thus, when pressurized air is introduced into the first port 84, the air acts on the piston 76 to cause the piston to move in the bore 78 from the opposite end towards the one end of the first air cylinder 74. This in turn, urges the resilient seal 82 to engage the top end 8 of the filter element 4 and causes the bottom end 6 of the filter element 4 to engage the resilient seal 72 mounted in the base member 62. Thus, a fluid tight seal is provided on the top end 8 and the bottom end 6 of the filter element 4 when the filter element 4 is acted on by the first air cylinder 74 in the filter holder element 60.

To release the filter element 4 from the filter holder member 60, the first port 84 is vented to atmosphere and pressurized air is introduced into the second port 86 thereby causing the piston 76 to move vertically in the bore 78 toward the one end. This causes the resilient seal member 82 to disengage from the top end 8 of the filter element 4 and to move a sufficient distance from the top end 8 to permit the removal of a filter element 4 from the filter holder member 60.

Each filter holder member 60 has a sample member 90 of which one will be described in detail. The sample member 90 includes an annular ring member 92 with three equally spaced apertures 93 (only one shown) formed axially therethrough. Each of the apertures 93 is positioned between the inner diameter 94 and the outer diameter 96 of the annular ring member 92. One of the three vertical support members 64 passes through one of the three apertures 93 such that the annular ring member 92 is guided by the vertical support member 64 as the annular ring member 92 moves vertically relative to the base member 62 and the top member 68. The annular ring member 92 further has an internal cavity 98 which forms a circular chamber between the inner diameter 94 and the outer diameter 96. The annular ring member has a plurality of equally spaced apertures 99 formed radially from the inner diameter 94 so as to communicate with the internal cavity 98.

The sample member 90 is moved vertically from the base member 62 by a second air cylinder 89 which is similar in construction to the first air cylinder 74. The second air cylinder 89 has a first port 87 adjacent to its one end and a second port 88 adjacent to its opposite end. When the first port 87 is connected to a pressurized air source, the air acts on the piston to cause the piston to move in the bore from the one end to the opposite end in the second air cylinder 89. The axial length of the rod of the second air cylinder 89 is selected to permit the piston to move the sampler member axially along the length of the filter element 4 such that the sampler member 90 moves vertically toward the top member 68 from the bottom end 6 to the top end 8 of the filter elememt 4. When the piston of the second air cylinder positions the sampler member 90 vertically toward the top member 68 and adjacent to the top end 8 of the filter element 4, the first port 87 is vented to atmosphere and pressurized air is introduced into the second port 88 of the second air cylinder 89 thereby causing the piston to move in the bore towards the opposite end. Thus, the sampler member 90 is made to move vertically along the axial length of the filter element 4 from the bottom end 6 to the top end 8 and to return to the bottom end 6. The sampler member 90 further has a port 97 mounted to the annular ring member 92 on its outer diameter 96 for flow communication with the internal cavity 98 therein. The port 97 is connected by means of a flexible hose 91 for a purpose to be described later on herein. The flexible hose 91 provides a flexible connection with the port 97 of the annular ring member 92 when the sampler member 90 moves axially along the length of the filter element 4.

FIG. 5 shows the pneumatic hookup of the apparatus 100 according to my invention. A pressurized air source (not shown) is connected to a water filter 102 to remove moisture from the air. A first conduit 104 connects the water filter 102 to a first pressure regulator 106. In the preferred embodiment, the air pressure is regulated to provide 30 p.s.i.g. air downstream of the first pressure regulator 106. One leg of a first tee 108 is connected to the first pressure regulator 106. The other leg of the first tee 108 is connected to a second pressure regulator 110. In the preferred embodiment, the second pressure regulator reduces the air pressure to 7 p.s.i.g. The second pressure regulator 110 is then connected to one leg of a second tee 112. The other leg of the second tee 112 is connected to a third conduit 114. The third conduit 114 is connected to one leg of a third tee 116. The branch leg of the third tee 116 is connected to a third solenoid 118 which is suitably connected by means of a fourth conduit 119 to the first port 84 of the first air cylinder 74 of the one of the pair of filter holder members 60 as shown in FIG. 3. The other leg of the third tee 116 is connected to a fourth tee 121. The branch of the fourth tee 121 is connected to a fourth solenoid 123 which is suitably connected by means of a fifth conduit 125 to the second port 86 of the first air cylinder 74 of the one of the pair of filter holder members 60 as shown in FIG. 3. The leg of the fourth tee 121 is connected to a fifth tee 127. The branch of the fifth tee is connected to a fifth solenoid 129 which is suitably connected by means of a sixth conduit 131 to a first port of the other of the pair of sample holder members 60. The other leg of the fifth tee 127 is then connected by means of a seventh conduit 133 to a sixth solenoid 135 which is then suitably connected by means of an eighth conduit 137 to a second port of the first air cylinder 74 of the other of the pair of filter holder members 60.

The branch of the first tee 108 is connected by means of a ninth conduit 139 to a lubricator 140. The lubricator 140 adds a predetermined amount of lubrication into the air in order to provide lubrication for moving parts downstream of the lubricator. The lubricator 140 is connected by means of a tenth conduit 141 to a sixth tee 143. The branch of the sixth tee 143 is connected to a first second air cylinder controller 145 for the one of the pair of filter holder members 60 which has a conduit 147 and a conduit 149 eminating therefrom. The second air cylinder controller functions to divert air alternatively into one conduit 147, or the other conduit 149. The one conduit 147 is connected to the first port 87 of the second air cylinder 89, as shown in FIG. 3. The other conduit 149 is connected to the second port 88 of the second air cylinder 89, also shown in FIG. 3. As discussed previously, the second air cylinder 89 causes the sampler member 90 to move vertically up and down relative to the base member 62. The second air cylinder controller 145 diverts the air from the one conduit 147 to the other conduit 149 in response to a first microswitch 57 mounted to the top member 68 or the second microswitch 59 which is mounted to the base member 62 as shown in FIG. 3. Thus, as the sampler member 90 rises vertically and is adjacent to the top end 8 of the filter element 4, the sampler member 90 trips the first microswitch 57 so as to send out an electrical impulse causing the second air cylinder controller 145 to respond by diverting the air from the one conduit 147 to the second conduit 149. This, in turn, causes the sampler member 90 to reverse direction so as to move towards the base member 62. When the sampler member 90 is adjacent to the bottom end 6 of the filter element 4, the sampler member actuates a second microswitch 59 which diverts the air from the other conduit 149 back to the first conduit 147.

Returning back to FIG. 5, the other leg of the sixth tee 143 is connected by means of an eleventh conduit 151 to a first air cylinder controller 155 for the other of the pair of sample holder members 60 which diverts air alternately into a conduit 157 and a conduit 159 in a similar fashion as the second air cylinder controller 145.

The branch of the second tee 112 is connected by means of a twelfth conduit 161 to a needle valve 163. The needle valve 163 regulates the flow of air therethrough. The needle valve 163 is connected by means of a conduit 165 to a filter element 167. The filter element 167 is a high efficiency particle separator so that virtually clean air passes downstream of the filter element. The filter 167 is then connected to one leg of a seventh tee 169. The branch of the seventh tee 169 is connected to a normaly open solenoid 171. The solenoid 171 is then connected to an eighth tee 173. The branch of the eighth tee 173 is then connected to the flexible hose 91 which is then connected to the sampler member 90 as previously described. The other leg of the eighth tee 173 is then connected to a seventh solenoid 175 for a purpose to be described later on herein.

The other leg of the seventh tee 169 is connected to a second normally open solenoid 177 which is then connected to a ninth tee 178. The branch of the ninth tee 178 is connected to a second sampler member similar to that previously described for the first sampler member 90. The other leg of the ninth tee 178 is connected to an eighth solenoid 179. The eighth solenoid 179 is connected to one leg of a tenth tee 181. The branch leg of the tenth tee 181 is connected to the seventh solenoid 175. The other leg of the tenth tee 181 is connected to an other branch of the cross 42. As previously described, the other leg of the cross 42 is connected to the first solenoid valve 51 and the one branch of the cross 42 is connected to the second solenoid valve 53. As also previously discussed, the one leg of the cross 42 is connected to the first conduit 41 thence to the detector device 30 which is connected by means of a second conduit 43 to a vacuum pump 48.

The various solenoids to actuate the first air cylinder and the air cylinder controllers for the second air cylinder as well as for drawing samples from the sampler member 90 are sequenced utilizing electric means (not shown) and timers (not shown) to energize and de-energize the various solenoid valves described herein are well known in the art.

In addition, an exhaust fan (not shown) may be optionally provided to draw any unwanted particles and dirt away from the filter holder member 60 and the filter element 4 to be tested. Thus, a clean environment is provided for testing the filter elements 4 which does not require operator skill and which is suitable for testing large numbers of filters as the quality control device on a production line. Those skilled in the art will recognize that the time required to test each filter element, the acceptable level reading on the meter 44 and the time to perform such testing can all be varied within the scope of the present invention. In addition, the number of filters which can be simultaneously tested at any one time is not limited to two filter elements.

OPERATION

Before operating the apparatus 100, liquid dioctyl phthalate is poured into the generator 11 of the smoke generator 10 and the amplifier circuits of the detector device 30 connected to suitable electric source means (not shown). A suitable source of air (not shown) is hooked up to the water filter 102, thence into the first pressure regulator 106 which is set to 30 p.s.i.g. From the first pressure regulator 106, the air then flows through the lubricator 140 and thence into the first and second air cylinder controllers 155 and 145 respectively. A portion of the air from the first regulator 106 passes through a second regulator 110 where the air pressure is regulated to 7 p.s.i.g. From the second regulator, the air then flows through the third conduit 114 and thence into solenoid valves 118, 123, 129 and 135 respectively for a purpose to be described later on herein. A portion of the air from the second regulator 110 also flows into the twelfth conduit 161 where it passes through a needle valve 163 where the air flow is throttled by conventional means. The air passing through the needle valve 163 then passes through a filter element 167 and thence into the seventh tee 169 where a portion of the air is diverted in through a normally open solenoid 171. From the solenoid 171, the air passes through an eighth tee 173 which has its one branch connected by a flexible hose 91 to the annular ring member 92 to purge clean air into the internal cavity 98 and thence out the apertures 99. The other leg of the seventh tee 169 passes through a second normally open solenoid 177 and thence through a ninth tee 178 into the second filter sampler member to purge the annular ring as previously described for the first filter sampler member 90. The other leg of the eighth tee 173 is then connected to the seventh solenoid 175 which is normally closed. In a similar manner, the other leg of the ninth tee 178 is connected to the eight solenoid 179 which is also normally closed. The solenoids 175, 179 respectively are connected by means of a tenth tee 181 to the other branch of the cross 42. The other leg of the cross 42 is connected to a first normally open solenoid valve 51 which is then connected to a particulate filter member 55 which is vented to atmosphere. The one branch of the cross 42 is connected to a second normally closed solenoid valve 53 which is connected to the outlet tube 19 to the impactor 14 of the smoke generator 10. The one leg of the cross 42 is connected by means of a first conduit 41 to the detector device 30 which is then connected by means of a second conduit 43 to a vacuum pump 48. When the detector device 30 is hooked up to suitable electric means (not shown), the vacuum pump is actuated to draw a sample in through the first conduit 41 into the detector device 30 as previously described.

With the solenoid valves 53, 175 and 179 closed, air is drawn through the particulate filter member 55, thence through the first solenoid valve 51, thence into the cross 42 and finally into the first conduit 41 and thence into the detector device 30 in order to calibrate the detector device 30. The meter 44 is then set to zero on the meter scale since clean air is being drawn into the detector device 30. Next, to calibrate the meter 44 on full scale or 100%, the normally open first solenoid valve 51 is closed and the normally closed second solenoid valve 53 is open to draw 100% D.O.P. smoke through the outlet tube 19 from the impactor 14 into the detector device 30. Next, the second solenoid valve 53 is closed which automatically opens the first solenoid valve 51 to draw clean air into the detector device 30 again and the meter is adjusted for stray light to zero on the meter scale 44.

While the apparatus includes a pair of filter test holder members 60, only one will be described in detail insofar as its operation, since the operation of the other filter holder is identical except as noted hereinafter. First, a filter element 4 is placed with its bottom end 6 centrally positioned on the resilient seal 72 with its top end 8 centrally disposed with the resilient seal 82 on the plate member 81 and with the central passage 5 centrally disposed in the filter holder member 60. The third solenoid 118 is then actuated to permit air to flow from conduit 114 through the third tee 116 into the fourth conduit 119 and thence into the first port 84 of the first air cylinder 74. Thus, the piston 76 is caused to move towards the top end 8 of the filter element 4. The piston 76 therefore moves the rod 77 with the resilient seal 82 and the plate 81 to come into contact with the top end 8 of the filter element 4 and pushes the filter element into contact with the resilient seal 72. Thus, the filter element 4 is sealed between the two resilient seals 72, 82. Then D.O.P. smoke from the impactor 14 of the smoke generator 10 is permitted to flow through the conduit 75 past the solenoid valve 22 when opened and thence into the aperture 66 in the base member 62. Since both ends of the filter element are sealed, the 100% D.O.P. smoke flows into the central passage 5 of the filter element 4 which causes the smoke to pass through the filter element 4 outwardly along its periphery along the axial length between the bottom end and the top end. As this occurs, the second air cylinder controller 145 is activated to permit flow of air through the conduit 147 and thence into the first port 87 of the second air cylinder 89. This causes the piston to move in the bore and in turn causes the annular ring member 92 to move axially from the bottom end 6 of the filter element 4 to the top end 8 of the filter element 4. Then, the seventh solenoid 175 is opened, the eighth solenoid 179 is closed, and the normally open solenoid 171 closed so that 100% D.O.P. smoke passing through the filter element 4 is drawn into the apertures 99 and into the internal cavity 98 of the annular ring 92. The smoke then passes through the flexible base 91, into the tee 173, through the open solenoid 175, past the tenth tee 181, into the cross 42, into the first conduit 41 and thence into the detector device 30 for analysis. In doing so, the D.O.P. sample thus passes through a beam of light emanating from the light source 34 through the lens 36 which is then directed from the one side of the conical chamber 38 towards the first cell through the aperture 39. The light is reflected forwardly off any D.O.P. smoke particles in the sample and the light is then concentrated onto the photo-multiplier tube 40. The resulting signal from the photo-multiplier tube 40 is fed into an amplifier circuit of the detector device 30. The amplified circuit processes the signal into linear reading on the meter 44. This results in a measurement of the mass concentration of the particulate matter in the air or smoke. The meter 44 is also connected to an audible alarm which is preset to a given meter reading so that, should the meter reading exceed a predetermined level, the alarm will alert the operator. The sampler member 90, when it reaches the top end of the filter element 4, touches a 57 microswitch 57 which in turn causes the second air cylinder controller 145 to direct air into the conduit 149 and thence into the second port 86 and at the same time vent to atmosphere the air in the conduit 147. This causes the piston to reverse its direction in the bore so that the annular ring member 92 proceeds to move from the top end 8 of the filter to the bottom end 6 of the filter element 4. In the meantime, the detector device 30 is continually analyzing the smoke particles passing radially through the filter element 4 as the sampler member 90 moves vertically up and down relative to the base member 62. When the sampler member 90 reaches the bottom end 6 of the filter element 4, it touches a second microswitch 59 which terminates air flow through the conduit 149. Then the other pair of the filter test holder members 60 is activated, if desired, in a similar manner except that the first air cylinder controller 155 is activated and the solenoids 171, 175 and 177 are closed, and the eighth solenoid 179 opened to draw the sample from the second sampler.

In the preferred embodiment, the apparatus 100 is provided with a pair of filter holders 60 so that while one filter is being analyzed, the operator is unloading and loading a filter element into the second station making it ready for the next test. Those skilled in the art will recognize that the first filter holder station and the second holder station can be fitted with an electronic lock-out so that they cannot operate simultaneously. During the operation of either station, the operator can remove the filter element from the test station whose operation has been completed, return the filter element into a suitable receptacle, keeping failures in a separate bin and thus reload the test station with a filter element to be tested.

Those skilled in the art will recognize that a certain amount of smoke will pass through the filter element 4. However, a leak is detected when an unusually high reading is obtained on the meter 44. The high reading will depend on the filter element and the maximum acceptable reading for any filter configuration. In the preferred embodiment, by way of nonlimiting example, the meter reading is set at 50.

While the invention has been described in connection with the preferred embodiment and procedure, it will be understood that this is not intended to limit the invention to that embodiment and procedure. On the contrary it is intended to cover all alternatives, modifications and equivalents as may be included within the spirit and scope of the invention as defined in the appended claims.

What is claimed is:

1. The method of testing a fluid filter element for defects comprising the steps of:
    passing a test fluid having foreign particles entrained therein through a filter element to be tested;
    moving a probe adjacent to the periphery of and transversely across the longitudinal axis of said filter element to collect foreign particles passing through said filter element; and
    measuring the concentration of particles collected by said probe.

2. The method of testing as claimed in claim 1, further comprising the steps of:
    indicating the concentration of particles collected by said probe.

3. The method of testing as claimed in claim 1 wherein said probe comprises:
    an annular sampler member movably disposed adjacent to said filter member;
    sample drawing means within said sampler member; and
    particulate detector means interconnected with said sample drawing means for analyzing the particles of smoke passing through said filter element.

4. A filter element testing device comprising:
    a filter holder member including:
        a base member having portions defining a first hole therethrough;
        at least one vertical support member mounted to said base member and positioned adjacent to said first hole;
        a top member disposed above said base member and connected to said at least one vertical support member, said top member having a portion defining a second hole therethrough; and
        a first resilient seal mounted on said base member and centrally disposed relative to said first hole, said first resilient member further being disposed toward said top member;
    means, mounted to said filter holder member, for clamping said filter element therein;
    means for passing particles entrained in air through said filter element; and
    means for detecting the particles entrained in air along the axial length of the filter element which pass through said filter element.

5. A filter element testing device as claimed in claim 4 wherein said means for passing particles through said filter element further comprises:
    a smoke generator connected to said first hole in said base member for flow communication therebetween.

6. A filter element testing device as claimed in claim 5 wherein said smoke generator is a dioctyl phthalate smoke.

7. A filter element testing device as claimed in claim 4 wherein said detecting means further comprises:
    an annular sampler member disposed adjacent to said filter element and further between said base member and said top member, said annular sampler member having sample drawing means, an outer diameter and an inner diameter and means for connecting said sampler member to said at least one vertical support member; and
    particulate detector means, connected to said sample drawing means, for quantitatively analyzing the particles of smoke passing through said filter element.

8. A filter element testing device as claimed in claim 7 wherein said sample drawing means further comprises:
    a vacuum pump connected to said sampler member, said sampler member further having portions defining an annular cavity therein, a plurality of radial holes extending from said inner diameter and comunicating with said annular cavity; and a port mounted on said outer diameter and communicating with said annular cavity, said port connected to said vacuum pump.

9. A filter element testing device as claimed in claim 4 wherein said clamping means further comprises:

resilient seal means, mounted to said top member, for sealingly engaging the top end of said filter element and for sealingly engaging the bottom end of said filter element to said first resilient seal.

10. A filter device for detecting leaks comprising:
a filter holder member including:
  a base member;
  at least one vertical support member mounted to said base member; and
  a top member disposed above said base member and connected to said at least one vertical support member;
means, mounted to said filter holder member for clamping said filter between said base and top members;
a smoke generator connected to said filter and further passing smoke through said filter; and
means for detecting the smoke passed through said filter, said means comprising:
  an annular sampler member centrally disposed about said filter and further between said base member and said top member, said annular sampler having an outer diameter, an inner diameter and sampling means;
  a vacuum pump connected to said sampling means;
  means for moving said annular sampler member along the axial length of said filter so as to collect the smoke passing through said filter through said sampling means; and
  means for quantitatively analyzing the smoke passing through said filter.

11. A filter device as claimed in claim 10 wherein said detecting means further comprises:
means for indicating the quantity of smoke between a first predetermined level and a second predetermined level.

12. A filter element testing device utilizing particles entrained in air, said device comprising:
a filter holder member;
means, mounted in said filter holder member, for clamping said filter element therein;
means for passing particles entrained in air through said filter element; and
means, movably mounted transversely of said filter element, for detecting the particles entrained in air passing through said filter element.

13. The filter element testing device of claim 12 wherein said filter holder member further comprises:
a base member;
at least one vertical support member mounted to said base member; and
a top member disposed above said base member and connected to said at least one vertical support member.

14. The filter element testing device of claim 12 wherein said filter holder member further comprises:
a base member having portions defining a first hole therethrough;
at least one vertical support member mounted to said base member and positioned adjacent to said first hole; and
a top member disposed above said base member and connected to said at least one vertical support member.

15. A filter element testing device as claimed in claim 14 wherein said top member has a portion defining an aperture therethrough and further comprising:
a first resilient seal mounted on said base member and centrally disposed relative to said first hole, said first resilient member further being disposed toward said top member.

16. A filter element testing device as claimed in claim 15 wherein said clamping means further comprises:
resilient seal means, mounted to said top member, for sealingly engaging the top end of said filter element and for sealingly engaging the bottom end of said filter element to said first resilient seal.

17. A filter element testing device as claimed in claim 12 wherein said detecting means further comprises:
an annular sampler member disposed adjacent to said filter element and further between said base member and said top member, said annular sampler member having sample drawing means, an outer diameter and an inner diameter and means for connecting said sampler member to said at least one vertical support member; and
particulate detector means, connected to said sample drawing means, for quantitatively analyzing the particles of smoke passing through said filter element.

18. A filter element testing device as claimed in claim 17 wherein said sample drawing means further comprises:
a vacuum pump connected to said sample member, said sampler member further having portions defining an annular cavity therein, a plurality of radial holes extending from said inner diameter and communicating with said annular cavity; and
a port mounted on said outer diameter and communicating with said annular cavity, said port connected to said vacuum pump.

19. A filter element testing device as claimed in claim 12 wherein said means for passing particles through said filter element further comprises:
a smoke generator connected to said first hole in said base member for flow communication therebetween.

20. A filter element testing device as claimed in claim 19 wherein said smoke generator is a dioctyl phthalate smoke.

21. A filter device as claimed in claim 19 wherein said detecting means further comprises:
an annular sampler member centrally disposed about the filter and further between said base member and said top member, said annular sampler having an outer diameter, an inner diameter and sampling means;
a vacuum pump connected to said sampling means;
means for moving said annular sampler member along the axial length of the filter so as to collect the smoke passing through the filter through said sampling means; and
means for quantitatively analyzing the smoke passing through the filter.

22. A filter device as claimed in claim 21 wherein said detecting means further comprises:
means for indicating the quantity of smoke between a first predetermined level and a second predetermined level.

23. A filter device as claimed in claim 22 wherein said indicating means has a meter.

24. A filter device as claimed in claim 22 wherein said indicating means has audible alarm means.

25. A filter device as claimed in claim 22 wherein said first predetermined level is 0 and said second predetermined level is 100.

* * * * *

UNITED STATES PATENT AND TRADEMARK OFFICE
CERTIFICATE OF CORRECTION

PATENT NO. : 4,402,214

DATED : September 6, 1983

INVENTOR(S) : Morgan H. Morgan and Pamela T. Anders

It is certified that error appears in the above-identified patent and that said Letters Patent is hereby corrected as shown below:

Column 3, line 5, delete "filters" and insert ---- filter ----.

Column 3, line 27, delete the comma ",".

Column 7, line 35, after "60" insert a comma ---- , ----.

Column 7, line 41, after "60" insert a comma ---- , ----.

Column 8, line 33, after "filter" insert ---- element ----.

Column 10, line 28, before "conduit" insert ---- the third ----.

Column 10, line 58, delete "base 91" and insert ---- hose 91 ----.

Signed and Sealed this

First Day of May 1984

[SEAL]

Attest:

GERALD J. MOSSINGHOFF

*Attesting Officer*  *Commissioner of Patents and Trademarks*